United States Patent

Morman et al.

Patent Number: 5,932,497
Date of Patent: *Aug. 3, 1999

[54] BREATHABLE ELASTIC FILM AND LAMINATE

[75] Inventors: Michael Tod Morman, Alpharetta; Cindy Janja Milicevic, Cumming, both of Ga.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/929,758

[22] Filed: Sep. 15, 1997

[51] Int. Cl.$^6$ ................ B32B 5/16; B29H 7/20
[52] U.S. Cl. ............ 442/286; 442/59; 442/227; 604/385.2; 604/373; 264/41; 428/230
[58] Field of Search ............... 604/373, 385.2; 428/230; 442/59, 227, 286

[56] References Cited

U.S. PATENT DOCUMENTS

| | | |
|---|---|---|
| 3,870,593 | 3/1975 | Elton et al. . |
| 4,308,303 | 12/1981 | Mastroianni et al. ............ 428/90 |
| 4,347,844 | 9/1982 | Ohki et al. ............... 128/287 |
| 4,381,782 | 5/1983 | Mazurak et al. ............ 604/368 |
| 4,472,328 | 9/1984 | Sugimoto et al. ............ 264/41 |
| 4,613,643 | 9/1986 | Nakamura et al. . |
| 4,657,802 | 4/1987 | Mormon et al. ............ 428/152 |
| 4,663,220 | 5/1987 | Wisneski et al. ............ 428/221 |
| 4,704,114 | 11/1987 | Wilson et al. ............ 604/385 |
| 4,710,187 | 12/1987 | Boland et al. ............ 604/385 |
| 4,713,069 | 12/1987 | Wang et al. ............ 604/378 |
| 4,720,415 | 1/1988 | Vander Wielen et al. ............ 428/152 |
| 4,741,949 | 5/1988 | Morman et al. . |
| 4,758,239 | 7/1988 | Yeo et al. ............ 604/366 |
| 4,777,073 | 10/1988 | Sheth et al. ............ 428/155 |
| 4,828,556 | 5/1989 | Braun et al. ............ 604/365 |
| 4,842,596 | 6/1989 | Kielpikowski et al. . |
| 4,850,990 | 7/1989 | Huntoon et al. ............ 604/385.2 |
| 4,892,779 | 1/1990 | Leatherman et al. . |
| 4,902,553 | 2/1990 | Hwang et al. . |
| 4,981,747 | 1/1991 | Morman . |
| 5,036,551 | 8/1991 | Dailey et al. ............ 2/167 |
| 5,114,781 | 5/1992 | Morman . |
| 5,116,662 | 5/1992 | Morman . |
| 5,130,342 | 7/1992 | McAllister et al. ............ 521/61 |
| 5,226,992 | 7/1993 | Morman . |
| 5,278,272 | 1/1994 | Lai et al. ............ 526/348.5 |
| 5,336,545 | 8/1994 | Morman . |
| 5,498,463 | 3/1996 | McDowall et al. . |
| 5,529,830 | 6/1996 | Dutta et al. . |
| 5,540,976 | 7/1996 | Shawver et al. . |
| 5,560,974 | 10/1996 | Langley ............ 428/198 |
| 5,674,212 | 10/1997 | Osborn, III et al. ............ 604/385.2 |
| 5,695,868 | 12/1997 | McCormack et al. ............ 426/283 |
| 5,702,382 | 12/1997 | Osborn, III et al. ............ 604/385.2 |
| 5,713,884 | 2/1998 | Osborn, III et al. ............ 604/385.2 |
| 5,766,387 | 6/1998 | Wolf et al. ............ 156/62.4 |
| 5,769,838 | 6/1998 | Buell et al. ............ 604/396 |
| 5,770,663 | 6/1998 | Peifer et al. ............ 526/127 |
| 5,789,065 | 8/1998 | Haffner et al. ............ 428/152 |

FOREIGN PATENT DOCUMENTS

| | | |
|---|---|---|
| 309 073 | 3/1989 | European Pat. Off. . |
| 352 802 | 1/1990 | European Pat. Off. . |
| 779 325 | 6/1997 | European Pat. Off. . |
| 98/05502 | 2/1998 | WIPO . |

OTHER PUBLICATIONS

"Polyolefins gain higher performance from new catalyst technologies", by Robert E. Leaversuch. Modern Plastics, Oct. 1991.

"Metallo–organic Chemistry", Anthony J. Pearson. p. 310, 1985.

"Modified Atmosphere Packaging Quality: The Value of Metallocene Resins", Brant, Michiels, Halle and Erderly, 1995.

*Primary Examiner*—Marion McCamish
*Assistant Examiner*—Arti R. Singh
*Attorney, Agent, or Firm*—Pauley Petersen Kinne & Fejer

[57] ABSTRACT

A soft, breathable elastic laminate of an elastic film loaded with a filler having a particle size suitable for pore formation and stretched in at least two directions to form a plurality of micropores bonded to a nonwoven web. In accordance with one embodiment, the elastic film is water vapor impermeable prior to being stretched.

63 Claims, 1 Drawing Sheet

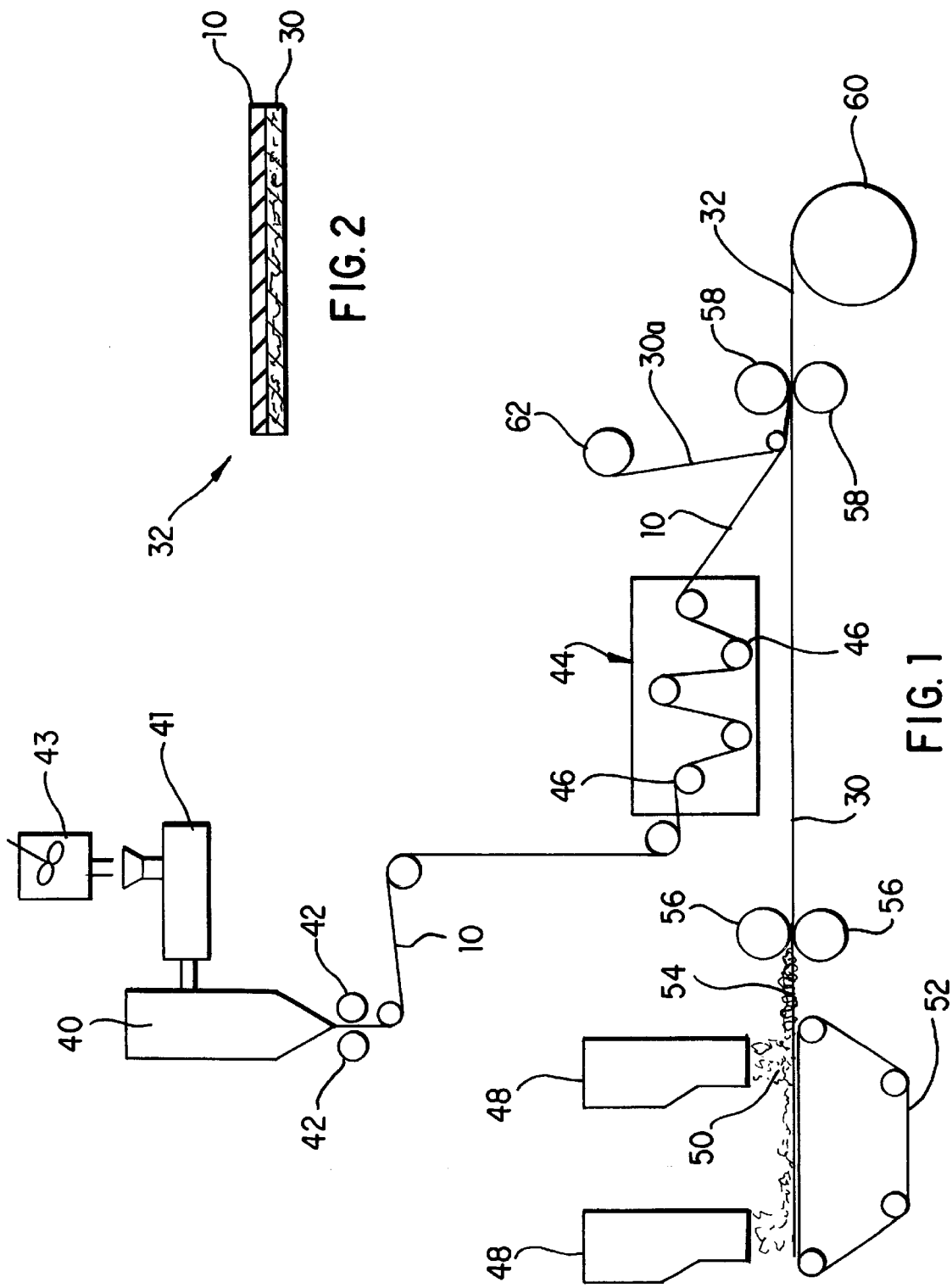

BREATHABLE ELASTIC FILM AND LAMINATE

FIELD OF THE INVENTION

This invention is related to a breathable elastomeric film and a soft, breathable elastic laminate comprising said breathable elastomeric film and a nonwoven web. The laminate is particularly useful as an outer cover for disposable diapers and other disposable personal care products, and for breathable surgical gowns and other breathable applications. In addition, this invention is also directed to a method for producing such laminates.

BACKGROUND OF THE INVENTION

The present invention is directed to breathable elastomeric films and nonwoven materials and laminates thereof. Such laminates have a wide variety of uses, particularly in the areas of limited use and disposable items.

Films have been traditionally used to provide barrier properties in limited use or disposable items. By limited use or disposable, we mean that the product and/or component is used only a small number of times, or possibly only once, before being discarded. Examples of such products include, but are not limited to, surgical and health care related products such as surgical drapes and gowns, disposable work wear such as coveralls and lab coats, and personal care absorbent products such as diapers, training pants, incontinence garments, sanitary napkins, bandages, wipes and the like. In personal care absorbent products, such as infant diapers and adult incontinence products, films are used as the outer covers so as to prevent body wastes from contaminating the clothing, bedding and other aspects of the surrounding environment of use. In protective apparel, such as hospital gowns, films are used to prevent cross exchange of microorganisms between the wearer and the patient.

Although these films are generally effective barriers with respect to water vapor and the like, they are not aesthetically pleasing because their surfaces are smooth and either feel slick or tacky and they are visually unappealing, making them less desirable in apparel applications and other uses where they are in contact with human skin. Thus, it is desirable that these items be more cloth-like, both from a tactile and visual standpoint. For example, infant diapers that have the feel and appearance of traditional cloth undergarments are perceived as premium products, overcoming the tendency in some cases to believe that they need to be covered by outer garments for aesthetic reasons. In addition, garment-like isolation gowns for use in hospital environments most likely would increase the comfort of the wearer while reducing the apprehensiveness of the patient. It is also preferable to provide an outer cover material with more elastic give and recovery to provide better fit and comfort.

Laminates of films have been used to create materials which are both impervious and somewhat cloth-like in appearance and texture. One example of such a laminate is the outer cover on disposable diapers.

A primary purpose of the film in such laminates is to provide barrier properties. However, there is also a need that such laminates be breathable so that they can transmit water vapor which, in turn, requires that the film be breathable. Apparel made from laminates of breathable or microporous films are more comfortable to wear because they reduce the water vapor concentration and the consequent skin hydration underneath the apparel item.

Accordingly, there is a need for an inexpensive laminate having a soft outer cover and good elastic and breathability properties which provides both cloth-like aesthetics and the fit and comfort desired by the wearer.

This invention is directed to films which do not inherently pass water vapor, but which are rendered porous to water vapor while remaining impermeable to liquid water, and to laminates employing such films. This invention is also directed to films which do inherently pass water vapor, for which the rate at which water vapor passes through is increased, and to laminates employing such films. Certain polymers, such as some polyurethanes, polyether esters, and polyether amides, inherently pass water vapor. The water vapor dissolves in the polymeric film, diffuses through the film, and evaporates from the other side. However, this diffusion process is often too slow, requiring that very thin films or specialty polymers be used to compensate. By loading the polymer with a filler material and stretching the resulting film so as to form micropores in the film in accordance with this invention, water vapor transport therethrough can be increased.

SUMMARY OF THE INVENTION

Various types of vapor permeable, liquid impermeable polymeric films are known in the art. This invention relates to a soft, breathable elastic laminate comprising a water vapor impermeable, or water vapor permeable, elastic film material loaded with a filler having a particle size suitable for pore formation and a nonwoven web bonded to the elastic film, the film being stretched in at least two directions. The stretching of the film renders the film microporous and, thus, breathable, or, in the case of films which are initially breathable, more breathable. The breathable elastomeric film in accordance with one embodiment is preferably a metallocene polyethylene polymeric resin material comprising a filler material of at least 10% by volume of the film. Preferably, the metallocene polyethylene polymeric resin material has a density of from about 0.850 to about 0.917 g/cc. Preferably, the film comprises from about 10% by volume to about 50% by volume filler.

In accordance with one embodiment of this invention, the polymeric resin material is selected from the group consisting of copolymers of ethylene and butylene, copolymers of ethylene and hexene, copolymers of ethylene and octene, and combinations thereof. To render the elastic film breathable, the film is stretched, causing voids to form in the film. The film may also be heated. The resulting breathable film has an activation permanent set, where permanent set is defined as the final or recovery length of the film less the initial length divided by the initial length×100, of greater than about 50%.

This invention is also directed to a process for producing a soft, breathable, elastic laminate in which a water vapor impermeable elastic film comprising a polymeric resin such as a metallocene polyethylene polymeric material and a filler having a particle size suitable for pore formation is stretched in at least two directions so as to form a plurality of micropores, after which the now water vapor permeable elastic film is bonded to a nonwoven web, forming a laminate. In accordance with one preferred embodiment of this invention, the film is stretched to a length in the range of 200 to 500% of its initial length. The resulting film has a water vapor transmission rate (WVTR) of at least about 400 grams per square meter per 24 hours (g/m$^2$/24 hrs.) (measured by ASTM Standard Test E96-80 with CELGARD® 2500 as control) and more preferably in the range of about 1000 to about 5000 g/m$^2$/24 hr.

A hypothetical example is a water vapor permeable elastic polyurethane film having a basis weight of approximately 30 g/m² and a WVTR of 1000 g/m²/24 hours. By loading the polymer with filler so as to form a film comprising 72.5 volume percent polymer and 27.5 volume percent filler, such as CaCO₃, and stretching the film to form micropores in accordance with this invention, a film is formed having a polymer basis weight of 30 g/m² and a WVTR of greater than about 1500 g/m²/24 hours may be formed, thereby substantially improving the WVTR.

Laminates of this invention have a wide variety of uses including, but not limited to, applications in personal care absorbent articles including diapers, training pants, sanitary napkins, incontinence devices, bandages and the like. These same laminates may also be used in items such as surgical drapes and gowns, as well as various articles of clothing, either the entire article or simply as a component thereof.

It is, thus, an object of this invention to provide an inexpensive laminate for use in personal care absorbent articles, surgical drapes and gowns, and various articles of clothing that has a soft outer cover and good elastic and breathability properties.

BRIEF DESCRIPTION OF THE DRAWINGS

These and other objects and features of this invention will be better understood from the following detailed description taken in conjunction with the drawings wherein:

FIG. 1 is a schematic side view of a process for forming a laminate in accordance with one embodiment of this invention; and FIG. 2 is a cross-sectional view of a laminate of this invention.

DEFINITIONS

The term "elastic" is used herein to mean any material which, upon application of a biasing force, is stretchable, that is elongatable, to a stretched, bias length which is at least about 150% of its relaxed unbiased length, and which will recover at least 50% of its elongation upon release of the stretching, elongating force. A hypothetical example would be a one (1) inch sample of a material which is elongatable to at least 1.50 inches and which, upon being elongated to 1.50 inches and released, will recover to a length of not more than 1.25 inches. Many elastic materials may be stretched by more than 50% of their relaxed length, for example, 100% or more, and many of these will recover to substantially their original relaxed length, for example, to within 105% of their original relaxed length, upon release of the stretching force.

As used herein, the term "breathable" refers to a film or laminate having water vapor transmission rate (WVTR) of at least about 300 g/m²/24 hours measured using ASTM Standard E96-80, upright cup method, with minor variations as described in the Test Procedure below.

As used herein, the term "substantially water vapor impermeable elastic film" means an elastic film having a water vapor transmission rate in an unstretched condition of less than about 100 g/m²/24 hours.

As used herein, the term "permanent set" refers to a final length of a stretched material upon termination of a biasing force following stretching of the material by application of the biasing force. For example, if a material having a relaxed, unbiased length of two (2) inches is elongated 400% by stretching to a length of ten (10) inches, and, if upon termination of the biasing force the material contracts to a final length of four (4) inches, then the permanent set for this material would be 100%. Permanent set may be expressed as [(final film length−initial film length)/initial film length]×100.

As used herein, the term "nonwoven web" means a web that has a structure of individual fibers or threads which are interlaid, but not in an identifiable, repeating manner. Nonwoven webs have been, in the past, formed by a variety of processes such as, for example, melt-blowing processes, spunbonding processes, and bonded carded web processes.

As used herein, the term "spunbonded fibers" refers to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or well-known spunbonding mechanisms.

As used herein, the term "necked material" refers to any material which has been narrowed in at least one dimension by application of a tensioning force in another direction.

As used herein, the term "neckable material" means any material which can be necked.

As used herein, the term "polymer" generally includes, but is not limited to, homopolymers, copolymers, such as for example, block, graft, random and alternating copolymers, terpolymers, etc., and blends and modifications thereof. Furthermore, unless otherwise specifically limited, the term "polymer" includes all possible geometrical configurations of the material. These configurations include, but are not limited to, isotactic, syndiotactic, and random symmetries.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solvents, particulates, and materials added to enhance processability of the composition.

TEST PROCEDURE FOR MEASURING WATER VAPOR TRANSMISSION RATE (WVTR)

A measure of the breathability of a fabric is the water vapor transmission rate (WVTR) which, for sample materials, is calculated essentially in accordance with ASTM Standard E96-80 with minor variations in test procedure as set forth hereinbelow. Circular samples measuring three inches in diameter are cut from each of the test materials, and tested along with a control, which is a piece of CELGARD® 2500 sheet from Celanese Separation Products of Charlotte, N.C. CELGARD® 2500 sheet is a microporous polypropylene sheet. Three samples are prepared for each material. The test dish is a No. 60-1 Vapometer pan distributed by Thwing-Albert Instrument Company of Philadelphia, Pennsylvania. 100 milliliters of water is poured into each Vapometer pan and individual samples of the test materials and control material are placed across the open tops of the individual pans. Screw-on flanges are tightened to form a seal along the edges of the pan, leaving the associated test material or control material exposed to the ambient atmosphere over a 6.5 cm diameter circle having an exposed area of approximately 33.17 square centimeters. The pans are placed in a forced air oven at 100° F. (32° C.) for one hour to equilibrate. The oven is a constant temperature oven with external air circulating through it to prevent water vapor accumulation inside. A suitable forced air oven is, for example, a Blue M Power-O-Matic 600 oven distributed by Blue M Electric Company of Blue Island, Ill. Upon completion of the equilibration, the pans are removed from the oven, weighed and immediately returned to the oven. After 24 hours, the pans are removed from the oven and weighed again. The preliminary test water vapor transmission rate values are calculated as follows:

Test WVTR=(grams weight loss over 24 hours)×315.5 g/m²/24 hours)

The relative humidity within the oven is not specifically controlled.

Under predetermined set conditions of 100° F. (32° C.) and ambient relative humidity, the WVTR for the CELGARD® 2500 control has been defined to be 5000 grams per square meter for 24 hours. Accordingly, the control sample was run with each test and the preliminary test values were corrected to set conditions using the following equation:

$$WVTR=(test\ WVTR/control\ WVTR)\times(5000\ g/m^2/24\ hrs.)$$

DESCRIPTION OF PREFERRED EMBODIMENTS

This invention is directed to breathable elastomeric films and to soft, breathable elastic laminates comprising said breathable elastomeric films. In accordance with one preferred embodiment, said breathable elastomeric films comprise metallocene ethylene-based polymers. The term "metallocene ethylene-based polymers" as used herein includes those polymer materials that are produced by the polymerization of at least ethylene using metallocenes or constrained geometry catalysts, a class of organometallic complexes, as catalysts. For example, a common metallocene is ferrocene, a complex with a metal sandwiched between two cyclopentadienyl (Cp) ligands. Metallocene process catalysts include bis(n-butylcyclopentadienyl) titanium dichloride, bis(n-butylcyclopentadienyl) zirconium dichloride, bis(cyclopentadienyl) scandium chloride, bis(indenyl) zirconium dichloride, bis(methylcyclopentadienyl) titanium dichloride, bis(methylcyclopentadienyl) zirconium dichloride, cobaltocene, cyclopentadienyltitanium trichloride, ferrocene, hafnocene dichloride, isopropyl (cyclopentadienyl,-1-flourenyl) zirconium dichloride, molybdocene dichloride, nickelocene, niobocene dichloride, ruthenocene, titanocene dichloride, zirconocene chloride hydride, zirconocene dichloride, among others.

The metallocene ethylene-based polymers used in this invention provide stretch and recovery properties to the film. Preferably, the metallocene ethylene-based polymer is selected from copolymers of ethylene and 1-butene, copolymers of ethylene and 1-hexene, copolymers of ethylene and 1-octene and combinations thereof.

Suitable metallocene polyethylene elastomers are available in a variety of densities. Preferably, the metallocene polymer material used in the laminates of this invention has a density in the range of about 0.850 to about 0.917 g/cc. More preferably, the material used in the laminates of this invention has a density in the range of about 0.860 to about 0.910 g/cc, and even more preferably in the range of about 0.870 to about 0.900 g/cc. The melt index range of some suitable materials is between about 1 to about 15 dg per minute and advantageously may be in the range of from about 5 to about 10 dg per minute.

In addition to the polymeric material, the film layer also comprises a filler which enables development of micropores during stretching of the film. As used throughout the specification and claims, the term "filler" means particulates and other forms of materials which can be added to the polymer and which will not chemically interfere with or adversely affect the extruded film but is able to be uniformly dispersed throughout the film. Generally, the fillers will be in particulate form and usually will have somewhat of a spherical shape with average particle sizes in the range of about 0.50 to about 8 microns. In addition, the film will usually contain in the range of about 10 to 50 volume percent filler based upon the total volume of the film layer. Both organic and inorganic fillers are suitable for use in this invention provided that they do not interfere with the film formation process, the breathability of the resultant film, or its ability to bond to another layer such as a fibrous polyolefin nonwoven web.

Examples of suitable fillers include calcium carbonate ($CaCO_3$), various kinds of clay, silica ($SiO_2$), alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, kaolin, mica, carbon, calcium oxide, magnesium oxide, aluminum hydroxide, pulp powder, wood powder, cellulose derivative, polymer particles, chitin and chitin derivatives.

Generally, we have found that we can make a metallocene film breathable by loading it with calcium carbonate particles and stretching it four times its initial length once in the machine direction to make it microporous and then relaxing it. The resulting film has a WVTR of about 200 g/m²/24 hours and a permanent set of about 30%. Taking the above machine direction stretched/relaxed film and additionally stretching it once in the cross-machine direction four times its original length and relaxing it increases the WVTR to about 2500 g/m²/24 hours while reducing the cross-machine direction permanent set to about 10% in a subsequent 100% cross-machine direction stretch. We believe that elastomeric films made from "non-breathable" polymers such as metallocene films loaded with filler are made breathable by stretching the films in one direction, forming pores around the solid filler particles. The pores thus formed around the solid particles are long slits in the direction of stretching. When the elastic retracts after stretching, the slits partially close. The amount of this slit "healing", and the resulting reduction in breathability, is therefore partially dependent upon how much the film retracts. The higher the permanent length increase after activation stretching, that is the activation permanent set, the higher the amount of breathability retained.

We have also found that stretching the film once in one direction and then once again in another direction, preferably perpendicular to the direction of the first stretch, significantly aids in maintaining the breathability after the film has retracted. This may be due to the microporous holes formed by the two way stretching being more "circular" in shape, thereby allowing much better breathability.

In general, a process for forming an elastic film 10 filled with filler is shown in FIG. 1. Filled film 10 is formed from a film extrusion apparatus 40, such as a cast or blown unit. Typically, apparatus 40 includes extruder 41. Filled resin, including the polymeric material and filler is prepared in mixer 43 and directed to extruder 41. Film 10 is extruded into a pair of nip or chill rollers 42, one of which, if desired, may be patterned so as to impart an embossed pattern to the newly formed film 10.

From the film extrusion apparatus 40, filled film 10 is directed to a film stretching unit 44, such as a machine direction orienter. Film stretching unit 44 has a plurality of stretching rollers 46 moving at progressively faster speeds relative to the pair disposed before it. Rollers 46 apply an amount of stress, thereby progressively stretching filled film 10 to a stretch length in the machine direction of the film which is the direction of travel of filled film 10 through the process as shown in FIG. 1. Stretch rollers 46 may be heated for better processing. Preferably, film stretching unit 44 also includes rollers (not shown) upstream and/or downstream from stretch rollers 46 that can be used to preheat filled film 10 before orienting and/or annealing, or cooling, it after stretching.

At the stretched length, a plurality of micropores form in filled film 10. Preferably, the stretched length is from about 160 to about 900%, more preferably from about 200 to about 500% of the unbiased length of the film prior to stretching. If desired, filled film 10 is conveyed out of film stretching unit 44 so that the stress is removed, thereby allowing the stretched film 10 to relax.

In addition to improving breathability, we have also found that the elastic properties of films used in this invention are also improved by two-way stretching. As previously stated, the film is made microporous by a high degree of stretching in the machine direction. This stretch orients the elastomeric polymer molecules in the machine direction and produces machine direction oriented slits. The molecular orientation significantly improves machine direction elastic properties in subsequent stretching while deteriorating cross-direction elastic properties. Unfortunately, in use, the material of this invention is stretched in the cross-direction. Two direction stretching helps orient some of the polymer molecules in the cross-direction, reducing some of the first cycle high permanence set and stress decay tendencies. In addition, the more circular holes produced by two-way stretching reduce stress concentration observed in the slits.

We have also found that the elastic properties of the film are changed if the film is stretched, for example, in the machine direction and then in a cross-machine direction, or if stretched in a cross-machine direction followed by stretching in the machine direction. The extent of stretching of the film in the machine direction and/or cross-machine direction will also change film properties. It is further within the scope of the invention that the film could be stretched in three or more different directions. Preferably, the direction of the second stretching is perpendicular to the direction of the first stretching. The last stretching should be in the direction in which the material will be stretched in use.

In accordance with a preferred embodiment, the soft, breathable elastic laminate of this invention is produced by stretching the elastic film in the machine direction and the cross-machine direction, letting it relax, and laminating it to a necked spunbond. In accordance with another embodiment, the laminate is produced by stretching the film in a machine direction, and letting it relax, attaching a necked spunbond, stretching the laminate in a cross-machine direction, and relaxing the cross-machine direction stretch. In accordance with another embodiment, the film is stretched in a first direction followed by a second, preferably perpendicular direction and then stretched in a machine direction and a spunbond is attached to the film while stretched in the machine direction, and then relaxed. In accordance with yet another embodiment, the elastic film is stretched in a cross-machine direction, stretched in a machine direction and spunbond attached thereto while the elastic film is stretched, after which the laminate is relaxed. In accordance with yet another embodiment of this invention, the elastic film is stretched in a first direction followed by a second, preferably perpendicular, direction and a necked spunbond is attached thereto while said film is stretched in a machine direction.

Referring again to FIG. 1, a conventional fibrous nonwoven web forming apparatus 48, such as a pair of spunbond machines, is used to form a nonwoven web. The long, essentially continuous fibers 50 are deposited onto a forming wire 52 as an unbonded web 54 and the unbonded web 54 is then sent through a pair of bonding rolls 56 to bond the fibers together and increase the tear strength of the resultant web layer 30. To assist in bonding, one or both of the rolls may be heated. Typically, one of rolls 56 is also patterned so as to impart a discrete bond pattern with a prescribed bond surface area to web 30. Bonding rolls 56 will run at a lower surface speed than bonding rolls 58 to cause web 30 to neck. The resulting laminate 32 is then stretched in the cross-machine direction to provide improved breathability and elastic properties. The other roll is usually a smooth anvil roll, but this roll also may be patterned if so desired. Once filled film 10 has been sufficiently stretched and, if appropriate, relaxed and nonwoven web 30 has been formed, the two layers are brought together and laminated to one another using a pair of laminating rolls or other means 58. As in the case of bonding rolls 56, laminating rolls 58 may also be heated. Also, at least one of the rolls may be patterned to create a discrete bond pattern with a prescribed bond surface area for the resultant laminate 32. Generally, the maximum bond point surface area for a given area of surface on one side of laminate 32 will not exceed about 50% of the total surface area. Once laminate 32 exits laminating rolls 58, it may be wound up into rolls 60 for subsequent processing. Alternatively, laminate 32 may continue in-line for further processing or conversion.

While nonwoven web 30 and elastic film 10 shown in FIG. 1 were bonded together through thermal point bonding, alternative bonding means may be used. Suitable alternatives include, for example, adhesive bonding and the use of tackifiers. In adhesive bonding, an adhesive such as a hot melt adhesive is applied between the film and the web to bind the film and web together. The adhesive can be applied by, for example, melt spraying, printing, or melt flowing. Various types of adhesives are available, including those produced from amorphous polyalphaolefins, ethylene vinyl acetate-based hot melts, and Kraton® brand adhesives available from Shell Chemical of Houston, Texas and Rextac™ Brand Adhesives from Rexene of Odessa, Tex.

When bonding is accomplished using tackifiers, the tackifier may be incorporated into the film itself. The tackifier essentially serves to increase adhesion between the film and web layers. The film and web laminate may subsequently be thermally point-bonded, although generally very little heat is required because the tackifier tends to increase the pressure sensitivity of the film and a bond somewhat like an adhesive bond can be formed. Examples of useful tackifiers include Wingtack™ 95, available from Goodyear Tire & Rubber Company of Akron, Ohio, and Escorez™ 5300, available from Exxon Chemical Company of Houston, Tex. As previously indicated, the direction of elasticity in the laminate may be tailored based upon the state of the film, that is, whether it is relaxed or stretched, during bonding to the nonwoven web, as well as the physical property of the nonwoven web material. For example, if the film is relaxed prior to bonding and the support layer is extensible, such as a necked material, in the cross-machine direction ("CD"), then a laminate with both CD and machine-direction ("MD") stretch can be produced. In addition, if the film is bonded to a non-extensible nonwoven web layer while in a stretched state, then a laminate with a MD stretch can be produced.

Table 1 summarizes material properties for several films suitable for use in laminates of this invention. The base film used was a 100 gram per square meter, 27.5 volume percent calcium carbonate loaded EG8200 resin blown film from Dow Chemical.

TABLE 1

| | Material Making | | | | | Permanent Set after 100% CD |
|---|---|---|---|---|---|---|
| Order of Stretch | % Stretch to make microporous | Activation Permanent Set | Basis Weight (gsm) | WVTR (g/m²/24 hr) | Hydrostatic Head (mbar)* | stretch of microporous film |
| 1. MD | 400 | 158% | 61 | 264 | | 31% |
| 2. CD | 400 | 158% | 64 | 557 | | 8% |
| 3. MD | 870 | 350% | 43 | 1496 | | |
| 4. MD | 400 | 158% | 52 | 2380 | Sample burst before failure | 10.5% |
| CD | 400 | 158% | | | | |
| 5. CD | 400 | 162% | 42 | 2591 | | 28% |
| MD | 400 | 144% | | | | |

*The sample tested for hydrostatic head would be the worst case scenario for porosity issues, as stretching in both the MD and CD would cause the largest and most micropores. There were no holes detected in this sample.

From Table 1 it can clearly be seen that stretching of the elastic film in at least two directions substantially increases the water vapor transmission rate of the films and, thus, the laminate. The data in Table 1 also show the differences in elastic properties of the film based upon stretching of the elastic film in the machine direction followed by stretching in the cross-machine direction compared to stretching in the cross-machine direction followed by stretching in the machine direction. In particular, a film which is stretched first in the machine direction and then in the cross-machine direction is significantly more elastic in subsequent cross-machine direction stretches than an elastic film stretched first in the cross-machine direction followed by stretching in the machine direction as evidenced by the permanent set data. As a general rule, the last stretch of the elastic film should be in the direction in which elasticity is desired.

EXAMPLE

A 100 gram per square meter, 27.5 volume percent calcium carbonate loaded EG8200 resin blown film from Dow Chemical, which had a WVTR of 24 g/m2/24 hours, was biaxially oriented and evaluated for WVTR and cycle testing. Each sample was stretched 400% in the machine direction and held for 5 seconds. The samples were then stretched 0%, 50%, 100%, 150%, 250%, or 400% in the cross-machine direction as shown in the second column of Table 2. Each sample was held for five (5) seconds in the stretched position. The samples were then tested for water vapor transmission rate and/or cycle tested to 60% stretch to determine tensions and degree of permanent set. The results are shown in Table 2.

TABLE 2

| Material Making Cross Direction Stretch | Material Testing and Evaluation | | | | |
|---|---|---|---|---|---|
| | Basis Weight (g/m²) | WVTR (g/m²/24 hours) | 30% Extension Tension 1st Cycle (g) | 30% Retraction Tension 2nd Cycle (g) | Permanent Set after 6 Cycles |
| 0% | 64 | 135 | 428 | 134 | 16 |
| 50% | 65 | 196 | 400 | 141 | 13 |
| 100% | 65 | 832 | 408 | 173 | 9.5 |
| 150% | 65 | 1345 | 396 | 170 | 11 |
| 250% | 59 | 1837 | 415 | 200 | 9 |
| 400% | 53 | 1052 | 443 | 225 | 9 |

The data in Table 2 clearly show the benefits achieved by stretching the elastic film used in the laminate of this invention in a machine direction followed by stretching in a cross-machine direction. Films stretched in the machine direction only have an unacceptably low WVTR of about 135 g/m²/24 hours as well as a relatively low 30% retraction tension of 134 grams. As the amount of stretch in the cross-direction is increased, both the WVTR and the 30% retraction tension are seen to increase in value, particularly with respect to the baseline condition of no cross-machine direction stretch. Thus, after a stretch of 400% in the cross-machine direction, it can be seen that the retraction tension per unit of basis weight is essentially double the retraction tension per unit of basis weight for the film which has not been stretched in the cross-machine direction. Thus, by stretching the elastic film in at least two directions, preferably perpendicular to one another, the last stretch being in the direction in which the film will be stretched in use, the amount of material required for an elastic film having acceptable WVTR and retraction tension is substantially less than the amount of material required where stretching in only one direction is performed.

In summary, the data in Table 2 show that by stretching the elastic film in the cross-machine direction, the WVTR increases from 135 to 196 to 832 to 1345 g/m²/24 hours without changing the basis weight of the film. In addition, the permanent set decreases from 16% to 13% to 9.5% to 11%. The 30% second cycle retraction tension increases from 134 g to 141 g to 173 g to 170 g, also without changing the basis weight of the film.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A soft breathable elastic laminate comprising:
   a substantially water vapor impermeable elastic film loaded with a filler having a particle size suitable for pore formation, said film having a basis weight of at least about 42 gsm and having been stretched in at least two directions to form a plurality of micropores; and
   a nonwoven web bonded to said elastic film after stretching of said elastic film in at least one of said directions.

2. A soft, breathable elastic laminate comprising:
   a substantially water vapor impermeable elastic film loaded with a filler having a particle size suitable for pore formation, said film having been stretched in at least two directions to form a plurality of micropores; and
   a nonwoven web bonded to said elastic film after stretching of said elastic film in at least one of said directions.

3. A laminate in accordance with claim 2, wherein said two directions of stretch are perpendicular to one another.

4. A laminate in accordance with claim 2, wherein said elastic film is stretched in said second direction after bonding of said nonwoven web.

5. A laminate in accordance with claim 2, wherein said elastic film is stretched in said second direction prior to bonding of said nonwoven web.

6. A laminate in accordance with claim 2, wherein said nonwoven web is bonded to said elastic film while said elastic film is stretched in at least one of said two directions.

7. A laminate in accordance with claim 2, wherein said elastic film is annealed, said annealing occurring during said stretching of said film.

8. A laminate in accordance with claim 2, wherein said elastic film comprises a metallocene ethylene-based polymer.

9. A laminate in accordance with claim 8, wherein said metallocene ethylene-based polymer has a density in a range of about 0.850 to about 0.917 g/cc.

10. A laminate in accordance with claim 8, wherein said polymer is selected from the group consisting of copolymers of ethylene and butylene, copolymers of ethylene and hexene, copolymers of ethylene and octene, and combinations thereof.

11. A laminate in accordance with claim 2, wherein said filler comprises in a range of about 10% to about 50% by volume of said elastic film.

12. A laminate in accordance with claim 2, wherein said elastic film has an activation permanent set of greater than about 50%.

13. A laminate in accordance with claim 12, wherein said film has an activation permanent set in a range of about 100% to about 400%.

14. A laminate in accordance with claim 2, wherein said nonwoven web comprises a spunbond web.

15. A laminate in accordance with claim 14, wherein said spunbond web comprises polypropylene.

16. A laminate in accordance with claim 2 having an WTVR in a range of about 1000 to about 5000 $g/m^2/24$ hours.

17. A laminate in accordance with claim 2 further comprising a second nonwoven web.

18. A laminate in accordance with claim 2, wherein said filler is calcium carbonate.

19. A diaper outercover comprising:
   a substantially water vapor impermeable elastic film loaded with a filler having a particle size suitable for pore formation and stretched in at least two directions to form a plurality of micropores; and
   a nonwoven web bonded to said elastic film after stretching of said elastic film in at least one of said directions.

20. A surgical gown comprising:
   a substantially water vapor impermeable elastic film loaded with a filler having a particle size suitable for pore formation and stretched in at least two directions to form a plurality of micropores; and
   a nonwoven web bonded to said elastic film after stretching of said elastic film in at least one of said directions.

21. A breathable elastic film comprising:
   a substantially water vapor impermeable elastic film loaded with a filler having a particle size suitable for pore formation and stretched in at least two directions to form a plurality of micropores.

22. A film in accordance with claim 21, wherein said filler is calcium carbonate.

23. A film in accordance with claim 22, wherein said calcium carbonate comprises in a range of about 10% to about 50% by volume of said elastic film.

24. A film in accordance with claim 21 having a pore activation permanent set of greater than about 50%.

25. A film in accordance with claim 21, wherein said filler comprises in a range of about 10% to about 50% by volume of said elastic film.

26. A film in accordance with claim 21 having a permanent set after a last said stretching of less than about 30% in a direction of said last stretching.

27. A film in accordance with claim 21, wherein said substantially water vapor impermeable elastic film is stretched in a machine direction followed by stretching in a cross-machine direction.

28. A film in accordance with claim 21, wherein said substantially water vapor impermeable elastic film is stretched in a cross-machine direction followed by stretching in a machine direction.

29. A film in accordance with claim 21, wherein said substantially water vapor impermeable elastic film comprises a metallocene ethylene-based polymer.

30. A film in accordance with claim 29, wherein said metallocene ethylene-based polymer has a density in a range of about 0.850 to about 0.917 g/cc.

31. A film in accordance with claim 21, wherein said filler has an average said particle size in a range of about 0.5 to about 8 microns in diameter.

32. A film in accordance with claim 21, wherein a nonwoven web is bonded thereto, forming a film/nonwoven laminate.

33. A process for producing a soft, breathable elastic laminate comprising the steps of:
   stretching a substantially water vapor impermeable elastic film loaded with a filler having a particle size suitable for pore formation in at least two directions so as to form a plurality of micropores; and
   bonding a nonwoven web to said stretched elastic film, forming a laminate.

34. A process in accordance with claim 33, wherein said substantially water vapor impermeable elastic film is stretched in a machine direction followed by stretching in a cross-machine direction.

35. A process in accordance with claim 33, wherein said substantially water vapor impermeable elastic film is stretched in a cross-machine direction followed by stretching in a machine direction.

36. A process in accordance with claim 33, wherein said substantially water vapor impermeable elastic film comprises a metallocene ethylene-based polymer.

37. A process in accordance with claim 36, wherein said metallocene ethylene-based polymer has a density in a range of about 0.850 to about 0.917 g/cc.

38. A process in accordance with claim 33, wherein said filler comprises in a range of about 10% to about 50% by volume of said elastic film.

39. A process for producing a breathable elastomeric film comprising the steps of:
   stretching a substantially water vapor impermeable elastic film loaded with a filler having a particle size suitable for pore formation in at least two directions so as to form a plurality of micropores.

40. A process in accordance with claim 39, wherein said substantially water vapor impermeable elastic film is stretched in a machine direction followed by stretching in a cross-machine direction.

41. A process in accordance with claim 39, wherein said substantially water vapor impermeable elastic film is stretched in a cross-machine direction followed by stretching in a machine direction.

42. A process in accordance with claim 39, wherein said substantially water vapor impermeable elastic film comprises a metallocene ethylene-based polymer.

43. A process in accordance with claim 42, wherein said metallocene ethylene-based polymer has a density in a range of about 0.850 to about 0.917 g/cc.

44. A soft, breathable elastic laminate comprising:
   a substantially water vapor impermeable elastic film loaded with a filler having a particle size suitable for pore formation, said film having been stretched in at least two directions to form a plurality of micropores; and
   a neckable nonwoven web bonded to said elastic film after stretching of said elastic film in at least one of said directions.

45. A laminate in accordance with claim 44, wherein said neckable nonwoven web is necked prior to being bonded to said elastic film.

46. A laminate in accordance with claim 45, wherein said necked nonwoven web is bonded to said elastic film while said elastic film is stretched in a direction perpendicular to a necking direction.

47. A soft, breathable elastic laminate comprising:
   a substantially water vapor impermeable elastic film loaded with a filler having a particle size suitable for pore formation, said film having been stretched in at least two directions to form a plurality of micropores; and
   a necked nonwoven web bonded to said elastic film after stretching of said elastic film in at least one of said directions.

48. A laminate in accordance with claim 46, wherein said necked nonwoven web is bonded to said elastic film while said elastic film is stretched in a direction perpendicular to a necking direction.

49. A soft, breathable elastic laminate comprising:
   a substantially water vapor impermeable elastic film loaded with a filler having a particle size suitable for pore formation, said film having been stretched in at least two directions to form a plurality of micropores; and
   a necked spunbond bonded to said elastic film after stretching of said elastic film in said at least two directions.

50. A soft, breathable elastic laminate comprising:
   a substantially water vapor impermeable elastic film loaded with a filler having a particle size suitable for pore formation, said film having been stretched in at least two directions to form a plurality of micropores; and
   a necked spunbond bonded to said elastic film, whereby said film is stretched in a machine direction and said necked spunbond is bonded to said film after said stretching in said machine direction, forming said laminate, and said laminate is stretched in a cross-machine direction.

51. A soft, breathable elastic laminate comprising:
   a substantially water vapor impermeable elastic film loaded with a filler having a particle size suitable for pore formation, said film having been stretched in a machine direction and a cross-machine direction to form a plurality of micropores; and
   a spunbond bonded to said elastic film while said elastic film is stretched in said machine direction.

52. A soft, breathable elastic laminate comprising:
   a substantially water vapor impermeable elastic film loaded with a filler having a particle size suitable for pore formation, said film having been stretched in a machine direction and a cross-machine direction to form a plurality of micropores; and
   a spunbond bonded to said elastic film while said elastic film is stretched in said machine direction and said cross-machine direction.

53. A soft, breathable elastic laminate comprising:
   a substantially water vapor impermeable elastic film loaded with a filler having a particle size suitable for pore formation, said film having been stretched in a machine direction and a cross-machine direction to form a plurality of micropores; and
   a necked spunbond bonded to said elastic film while said elastic film is stretched in said machine direction.

54. A breathable elastic film comprising:
   an elastic film loaded with a filler having a particle size suitable for pore formation and stretched in at least two directions to form a plurality of micropores.

55. A breathable elastic film in accordance with claim 54, wherein said elastic film is substantially water vapor impermeable.

56. A breathable elastic film in accordance with claim 54, wherein said elastic film is water vapor permeable.

57. A film in accordance with claim 54, wherein said filler is calcium carbonate.

58. A film in accordance with claim 57, wherein said calcium carbonate comprises in a range of about 10% to about 50% by volume of said elastic film.

59. A film in accordance with claim 54, wherein said filler comprises in a range of about 10% to about 50% by volume of said elastic film.

60. A film in accordance with claim 54, wherein said elastic film is stretched in a machine direction followed by stretching in a cross-machine direction.

61. A film in accordance with claim 54, wherein said elastic film is stretched in a cross-machine direction followed by stretching in a machine direction.

62. A film in accordance with claim 54, wherein a nonwoven web is bonded thereto, forming a film/nonwoven laminate.

63. A film in accordance with claim 54, wherein the WVTR of said film is at least about 300 g/m$^2$/24 hours greater than the WVTR of said elastic film without said filler after being stretched the same as said elastic film loaded with said filler.

\* \* \* \* \*